US008141434B2

(12) United States Patent
Kippersund et al.

(10) Patent No.: US 8,141,434 B2
(45) Date of Patent: Mar. 27, 2012

(54) FLOW MEASURING APPARATUS

(75) Inventors: Remi Andre Kippersund, Bergen (NO);
Kjell Eivind Frøysa, Fyllingsdalen (NO); Per Lunde, Sandsli (NO)

(73) Assignee: TeCom AS, Bergen (NO)

( * ) Notice: Subject to any disclaimer, the term of this patent is extended or adjusted under 35 U.S.C. 154(b) by 0 days.

(21) Appl. No.: 12/800,081

(22) Filed: May 7, 2010

(65) Prior Publication Data

US 2011/0271769 A1    Nov. 10, 2011

(30) Foreign Application Priority Data

Dec. 21, 2009 (GB) .................................. 0922466.8
Dec. 22, 2009 (NO) .................................. 20073582

(51) Int. Cl.
*G01F 1/66* (2006.01)
(52) U.S. Cl. .................................. 73/861.28
(58) Field of Classification Search ... 73/861.25–861.28
See application file for complete search history.

(56) References Cited

U.S. PATENT DOCUMENTS

| | | | |
|---|---|---|---|
| 3,727,454 | A | 4/1973 | Courty |
| 3,727,458 | A | 4/1973 | Parkinson |
| 3,731,532 | A | 5/1973 | Courty |
| 3,783,169 | A | 1/1974 | Newhall |
| 4,015,470 | A | 4/1977 | Morrison |
| 4,118,983 | A * | 10/1978 | Brazhnikov ............... 73/290 V |
| 4,195,516 | A | 4/1980 | Fredericks |
| 4,454,767 | A | 6/1984 | Shinkai et al. |

(Continued)

FOREIGN PATENT DOCUMENTS

EP     1 6221 856 A2    2/2006
(Continued)

OTHER PUBLICATIONS

Examiner's Search Report under Section 17 for priority patent application No. GB0922466.8, dated Apr. 15, 2010.

*Primary Examiner* — Jewel V Thompson
(74) *Attorney, Agent, or Firm* — Abelman, Frayne & Schwab

(57) ABSTRACT

A flow measuring apparatus measures a fluid flow within a conduit including a wall. The apparatus includes a transducer arrangement including at least two transducers for alternately emitting and receiving ultrasonic radiation through the conduit wall and the flow. The apparatus also includes a signal processing arrangement for generating signals to excite the transducer arrangement and for processing received signals provided by the transducer arrangement for generating output signals from the signal processing arrangement indicative of properties of the flow. The transducer arrangement in cooperation with the conduit provides a first path for Lamb-wave ultrasonic radiation coupling directly from a first of the at least two transducers, to a second of said at least two transducers to generate a first received signal. The transducer arrangement in cooperation with the conduit provides at least one second path for ultrasonic propagation along the wall via Lamb waves coupling to at least a portion of the flow from a first of the at least two transducers to a second of the at least two transducers to generate a second received signal. The signal processing arrangement determines from said first and second received signals ultrasonic radiation propagation time periods through the first path and through the at least one second path, and to perform computational operations on the propagation time periods to determine properties of the flow including, but not limited to, at least one of: fluid flow velocity (v) in the conduit, a sound velocity (c) through the fluid.

16 Claims, 8 Drawing Sheets

U.S. PATENT DOCUMENTS

| | | |
|---|---|---|
| 4,467,659 A | 8/1984 | Baumoel |
| 4,735,097 A * | 4/1988 | Lynnworth ................ 73/861.28 |
| 4,748,857 A | 6/1988 | Nakagawa |
| 4,838,127 A * | 6/1989 | Herremans et al. ........ 73/861.28 |
| 4,930,358 A | 6/1990 | Motegi et al. |
| 5,040,415 A | 8/1991 | Barkhoudarian |
| 5,131,279 A * | 7/1992 | Lang et al. ................ 73/861.27 |
| 5,280,728 A * | 1/1994 | Sato et al. ................. 73/861.28 |
| 5,856,622 A | 1/1999 | Yamamoto et al. |
| 6,293,156 B1 | 9/2001 | Shen et al. |
| 6,550,342 B2 * | 4/2003 | Croteau et al. ................. 73/800 |
| 6,550,345 B1 * | 4/2003 | Letton ........................ 73/861.27 |
| 2007/0151364 A1 | 7/2007 | Wiest et al. |

FOREIGN PATENT DOCUMENTS

| | | |
|---|---|---|
| GB | 2343249 | 5/2000 |
| JP | 62100615 | 5/1987 |

* cited by examiner (PRIOR ART) FIG. 1

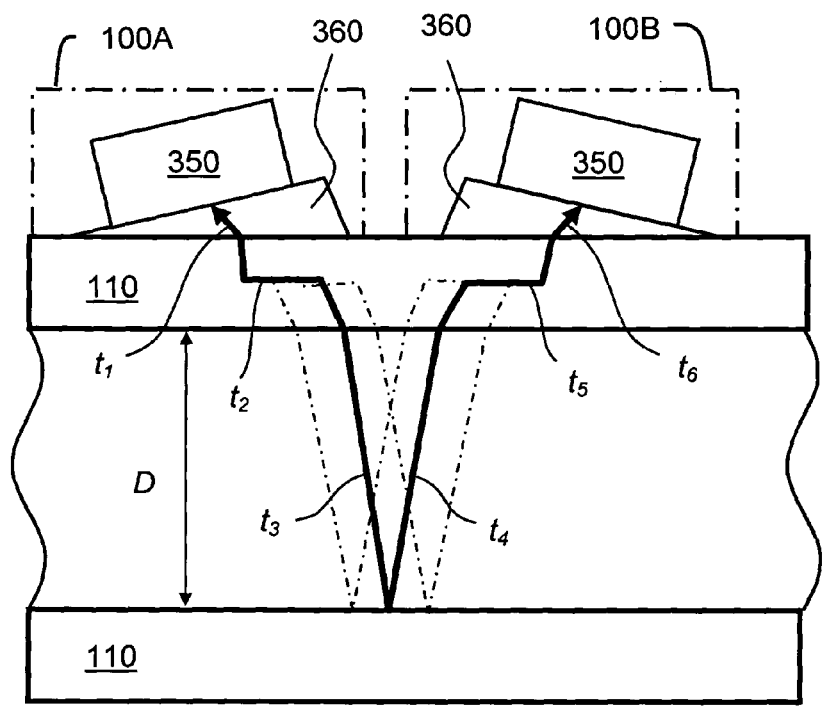
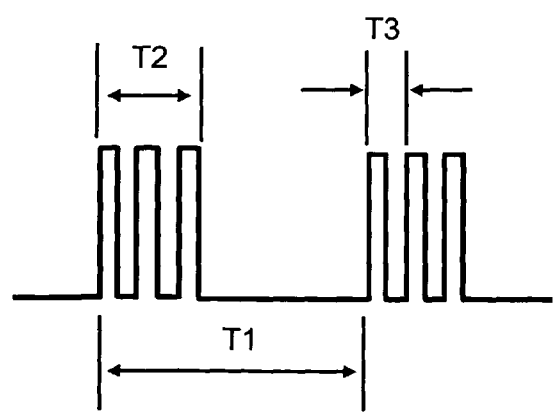
FIG. 4

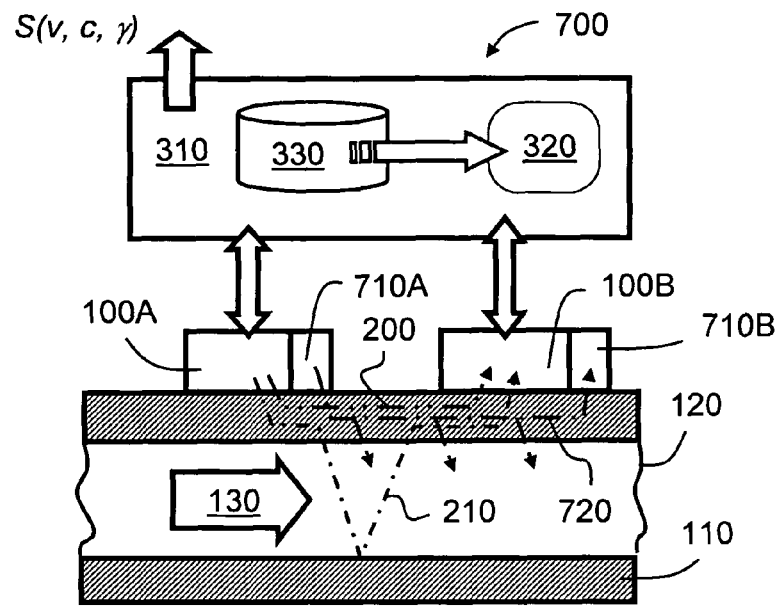
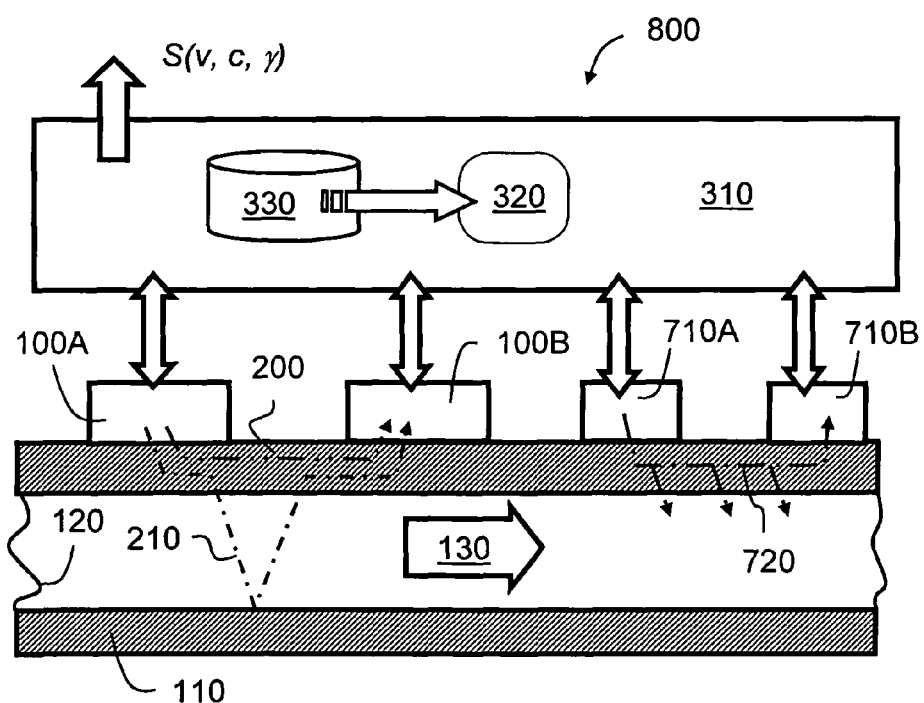
FIG. 8

FLOW MEASURING APPARATUS

TECHNICAL FIELD OF INVENTION

The present invention relates to flow measuring apparatus, for example to a flow measuring apparatus for measuring a flow velocity and a sound velocity of a fluid flowing through a conduit by utilizing at least two ultrasonic transducers mounted onto an outer surface of the conduit. Moreover, the invention relates to a method of measuring flow velocity and sound velocity of a fluid, for example to a method of measuring flow velocity and sound velocity in a fluid by utilizing at least two ultrasonic transducers mounted onto an outer surface of a conduit.

BACKGROUND TO THE INVENTION

Ultrasonic transit-time flow measurement is well known for measuring fluid flow velocities through conduits. Moreover, such flow measurement is feasible without introducing mechanical obstructions to the flow. In addition to an advantage of such non-obstructiveness, ultrasonic flow measuring apparatus often offer a relatively low cost of installation and operation. This is in particular true for apparatus that are clamped to an outside of conduits guiding flows of fluids in operation. Numerous methods and apparatus for ultrasonic flow measurement have been proposed and patented since the 1950's. A general review of ultrasonic flow measurement is to be found in Lynnworth & Liu, Ultrasonics 44, 2006, pp. 1371-1378.

In an ultrasonic flow measuring apparatus, at least one pair of ultrasonic transducers are configured at upstream and downstream positions relative to each other. The pair of transducers alternately transmits and receives ultrasonic signals that propagate along at least one path in a fluid to be characterized. Transit times of upstream- and downstream-propagating signals can be used to compute a flow velocity of the fluid.

FIG. 1 is an illustration of an example of a conventional known type of ultrasonic transit-time flow measuring apparatus mounted to a conduit 10. The apparatus employs a fixed acoustic propagation path 20 having a spatial extent from a first ultrasonic transducer 30 (A) via a region of fluid 40 at an angle $\phi$ relative to an elongate axis of the conduit 10, to a second transducer 50 (B). Firstly, an ultrasonic signal is sent in a first direction from the first transducer 30 via the region of fluid 40 to the transducer 50 (B). Secondly, an ultrasonic signal is then transmitted in the opposite direction, from the second transducer 50 (B) via the region of fluid 40 to the first transducer 30 (A). Thus, two transit times are measured for the first and second directions, namely $t_u$ for upstream ultrasonic signal propagation, and $t_d$ for downstream ultrasonic signal propagation. Assuming that the ultrasound signal velocity c is much greater than the fluid flow velocity v, namely $v^2 \ll c^2$, an inference of an axial flow velocity of the fluid in the region 40 can be derived from the transit times $t_u$, $t_d$ using Equation 1 (Eq. 1):

$$v = \frac{c^2 \tan\varphi}{2D}(t_u - t_d) \qquad \text{Eq. 1}$$

wherein D is a distance between inner surfaces of the conduit 10, for example a diameter of the conduit 10 when it has a round profile. The sound velocity c in the fluid and the angle $\phi$ between the wall of the conduit 10 and the direction of ultrasound propagation along the path 20 are previously determined quantities. A derivation of Equation 1 (Eq. 1) can be found in U.S. Pat. No. 5,856,622.

It is conventional to employ a model which regards the two transducers 30, 50 as points and ultrasonic radiation propagating as rays through these points. The diameter D and a distance L between the transducers 30, 50 determine an acoustic propagation path for propagation of the ultrasonic radiation. The ultrasonic transducers 30, 50 must be designed so that a main portion of ultrasonic radiation is radiated at an angle $\phi$ that causes the radiation to be received at a receiving transducer. As the ultrasonic propagation path is in reality affected by the temperatures of ultrasonic wedges employed for the transducers 30, 50, as well as temperatures of the conduit walls and velocities of the ultrasonic radiation and flow velocity v, a certain ultrasonic radiation beam width is necessary for the transmitted ultrasonic radiation to reach a receiving transducer 30, 50 as appropriate. Depending on beam width and departure from the theoretical model, ultrasonic radiation may propagate not only along the assumed path 20, but also simultaneously through multiple paths with transit times that differ slightly from the expected values. Such spurious paths influence a transit time measurement accuracy that can be achieved and are especially relevant when ultrasonic transducers are mounted on an external surface of a conduit. A method described in U.S. Pat. No. 4,930,358 for improving flow measurement accuracy is therefore based on reducing an angle of directivity and thus the number of spurious ultrasonic propagation paths. Reduced angles of directivity are typically accomplished by increasing the size and coupling surface area of ultrasonic transducers employed.

U.S. Pat. No. 5,856,622 discloses an iterative method for temperature and pressure compensation in the calculation of flow velocity from transit times measured using the aforementioned conventional method. Moreover, U.S. Pat. Nos. 4,195,516, 4,930,358 and 5,280,728 disclose transducer wedge portions that are designed to allow on-line measurement of the sound velocity of the wedge material. It is found that the sound velocity in the transducer wedge is important both with respect to transit times and with respect to an angle of refraction achieved into the liquid. Disclosures in these US patents indicate different ways to compensate for temporal uncertainties due to variable transducer delay and propagation path, which the conventional method is sensitive to, but they do not propose any approach to fully avoid any of these problems. U.S. Pat. No. 4,748,857 proposes an apparatus and a method wherein a mounting distance between transducers is altered to compensate for sound velocity changes in a fluid to be characterized. Such adjustments are impractical in many applications and potentially can give rise to increased apparatus cost, extra complexity and reduced reliability.

In a U.S. Pat. No. 4,454,767, there is described an apparatus including two ultrasonic transducers with wedges which are integrated into a single clamping mechanism to ensure proper mutual positioning of the transducers when the apparatus is mounted into an outer surface of a pipe. The apparatus may enable practical installation in a clamp-on manner, but does not compensate for measurement uncertainty due to variations in temperature and fluid composition.

A coherent multi-path flow measurement system is described in U.S. Pat. No. 6,293,156, the system being based upon transmission of a high-frequency ultrasonic beam into a wall of a steam- or gas-carrying pipe. This beam is reflected in operation from an inner and outer surface of a wall of the pipe and thus impinges on an inner wall at repeated locations separately axially by a skip distance. For each such incidence, a portion of the ultrasonic energy within the pipe is radiated into a flowing medium present in the pipe, thus forming multiple discrete ultrasonic propagation paths through the medium. A plurality of ultrasonic receivers are positioned to receive ultrasonic signals transmitted along different paths, and flow velocity of the medium is found by cross-correlation of the received signals. The flow measurement system is not a transit-time flow meter and is not subject to the same uncertainties as aforementioned conventional flow meters. However, the measurement system is subject to other uncertainties, namely related to the skip distance and ultrasonic beam width. Moreover, the measurement system may operate at frequencies which are too high for multiphase flow measurements, for example as pertinent to oil industries.

As Equation 1 (Eq. 1) indicates, accurate knowledge of the sound velocity c in the fluid is important for flow velocity measurement by the conventional method. The sound velocity c is also often a sought-after parameter for characterization of the fluid, and is generally obtained by undertaking separate measurements. For example, U.S. Pat. Nos. 3,731,532, 3,783, 169, 3,727,454, 3,727,458 and 4,015,470 disclose methods that employ three or four transducers to measure both flow and sound velocity. U.S. Pat. No. 5,040,415 discloses use of four transducers for measuring transit times for four paths through the fluid and therefrom infer flow velocity, temperature and pressure from the measurements. As the sound velocity of ultrasonic radiation in a fluid is generally pressure and temperature dependent, fluid characterization measurements must either be performed under the particular conditions of interest, or the temperature and pressure must also be measured and associated correction applied. Moreover, the sound velocity in a multiphase flow is strongly dependent upon fluid composition and may fluctuate rapidly as the fluid composition fluctuates. A need to add temperature and pressure measurement to conventional fluid flow measurement apparatus represents an added complexity and cost.

In U.S. Pat. Nos. 4,467,659 and 4,838,127, there are described designs for flow measuring apparatus that produce and detect Lamb guided-wave modes in a wall of a fluid-carrying conduit. The generated Lamb modes couple to the fluid flowing in the conduit so that ultrasonic signals follow paths for which measured transit times can be combined for calculating the flow velocity of the fluid. Moreover, in a U.S. Pat. No. 4,735,097, there are described ultrasonic transducers mounted onto a surface of a plate-like structure such as a fluid-carrying conduit, the transducers being operable to generate a Rayleigh-like disturbance at the remote surface of the wall. This disturbance functions as an extensive aperture which is several ultrasonic wavelengths wide in respect of an ultrasonic signal radiating into the fluid. A very short pulse is employed for generating such Rayleigh-like oscillations without exciting Lamb-modes. The aforementioned three patents are concerned with transducer design per se, and not flow velocity measurement.

From the foregoing, it will be appreciated that considerable technical effort has been devoted to develop and evolve ultrasonic flow measurement apparatus. Such effort has resulted in complex instruments which experience measurement accuracy difficulties when presented with complex flow mixtures, for example multiphase liquid/gas mixtures including particulate matter. Several approaches exist for compensating for measurement uncertainties inherent to the conventional method. However, hitherto, despite extensive effort as elucidated in the foregoing, no alternative methods have been disclosed that keep the advantages but avoid the aforementioned inherent uncertainty of ultrasonic transit-time flow measurement.

SUMMARY OF THE INVENTION

The present invention seeks to provide a more robust and simpler flow measuring apparatus for measuring at least flow velocity in fluids, for example in complex multiphase mixtures of fluids.

According to a first aspect of the invention, there is provided a flow measuring apparatus as defined in appended claim 1: there is provided a flow measuring apparatus for measuring a flow of a fluid within a conduit including one or more walls, the apparatus including a transducer arrangement including at least two transducers for alternately emitting and receiving ultrasonic signals, and a signal processing arrangement for generating signals to excite the transducer arrangement and for processing received signals provided by the transducer arrangement for generating output signals from the signal processing arrangement indicative of properties of the flow, characterized in that the transducer arrangement in cooperation with the conduit is operable to provide a first path solely via the one or more walls for Lamb-wave ultrasonic radiation coupling directly from at least one transducer emitting ultrasonic radiation to at least one transducer receiving ultrasonic radiation to generate a first received signal;

the transducer arrangement in cooperation with the conduit is operable to provide at least one second path for ultrasonic propagation within the one or more walls via Lamb waves coupling to at least a portion of the flow from at least one transducer emitting ultrasonic radiation to at least one transducer receiving ultrasonic radiation to generate a second received signal which propagates partly through the conduit wall and partly through the fluid; and the signal processing arrangement is operable to determine from the first and second signals ultrasonic radiation propagation time periods through the first path and through the at least one second path, and to perform computational operations on the propagation time periods to determine the properties of the flow in respect of at least one of: a flow velocity (v) of the fluid in the conduit, a velocity of sound (c) through the fluid.

The invention is of advantage in that:

(a) the flow measuring apparatus is operable to employ Lamb waves propagating in the one or more walls, which transmit ultrasonic energy to and receive ultrasonic energy from the fluid flow at any point between the at least two transducers; in consequence, the distance between a pair of transducers of the transducer arrangement is not a critical parameter for the sound propagation path; and (b) the first Lamb wave propagation path which is solely within the one or more conduit walls acts as a reference for enabling accurate and reliable measurement of fluid flow velocity and sound velocity to be achieved from ultrasonic pulse propagation time measurements.

Optionally, the flow measuring apparatus is operable to compute the flow velocity (v) of the fluid and/or the velocity (c) of sound in the fluid from the propagation time periods in combination with data relating to phase velocity of Lamb waves in the one or more walls of the conduit and a spatial dimension (D) of the conduit.

Optionally, the apparatus is operable to determine the ultrasonic radiation propagation time periods through the first path and through the at least one second path in upstream and downstream directions relative to the flow of fluid. More optionally, the apparatus is implemented such that the propagation time periods via a plurality of the at least one second path are temporally mutually similar so as to provide the signal processing unit with a single temporal pulse or pulse burst for performing time measurements for determining the fluid flow velocity (v) and/or the velocity of sound (c).

Optionally, the apparatus is adapted to include and/or be fitted to a section of the conduit having a substantially constant transverse dimension (D) in respect of an axial direction of the conduit in a region between transducers of the transducer arrangement, the constant transverse dimension (D) enabling propagation time delays via the at least one second path to be mutually temporally similar.

Optionally, the apparatus is implemented such that the conduit includes at least one flow restriction for generating a pressure difference thereacross in response to a fluid flow therethrough, and the apparatus further includes one or more pressure sensors for measuring the pressure difference developed across the at least one flow restriction and generating a pressure signal ($S_P$) indicative of the pressure difference for the signal processing arrangement, and a temperature sensor arrangement for measuring a temperature of the flow of fluid and/or temperature differences across pipe lengths or pipeline components for providing the signal processing arrangement with temperature signals ($S_T$) indicative of temperature, and the signal processing arrangement is operable to utilize any combination of one or more pressure measurements, one or more pressure difference measurements, one or more temperature measurements, one or more temperature difference measurements, one or more fluid flow velocity measurements and the mixture speed of sound to determine one or more fluid flow rates, one or more fluid fractions, and/or one or more fluid characteristics, for example viscosity and/or density of the fluid or fluid phases present.

Optionally, the apparatus is implemented such that the transducer arrangement includes a plurality of pairs of transducers for measuring spatially differential fluid flows within the conduit, for example, for increased robustness for, and/or corrections for, measuring fluid flow velocity profiles in the conduit or spatial phase distributions in the conduit if more than one fluid phase is present in the conduit.

Optionally, the apparatus is implemented such that the attenuation of the ultrasonic signal following the first path can be monitored to provide input to a frequency tuning arrangement for tuning operation of the apparatus for providing in operation optimal energy transfer between the transducer arrangement and the fluid.

Optionally, an attenuation measurement of radiation through the fluid in the conduit is used as a first measure of fluid density, based upon the attenuation of certain guided wave modes being substantially proportional to an acoustic impedance ratio between the fluid and the conduit.

Optionally, the apparatus is implemented such that the transducer arrangement in cooperation with the signal processing arrangement is operable to excite wave modes with essentially tangential motion on the surface of the one or more walls, these wave modes being of a nature to couple into the fluid in the conduit as a function of a viscosity of the fluid, and wherein the signal processing arrangement is operable to measure attenuation of these wave modes in the one or more walls for computing a viscosity of the fluid within the conduit.

According to a second aspect of the invention, there is provided a method of measuring a flow of a fluid within a conduit including one or more walls, characterized in that the method includes:

(a) arranging for a transducer arrangement to include at least two transducers for alternately emitting and receiving ultrasonic radiation propagated through the flow, and arranging for a signal processing arrangement to generate signals to excite the transducer arrangement and to process received signals provided by the transducer arrangement;

(b) providing for the transducer arrangement in cooperation with the conduit to provide a first path solely via the one or more walls for Lamb-wave ultrasonic radiation coupling directly from at least one transducer emitting ultrasonic radiation and at least one transducer receiving ultrasonic radiation to generate a first received signal;

(c) providing for the transducer arrangement in cooperation with the conduit to provide at least one second path for ultrasonic propagation within the one or more walls via Lamb waves coupling to at least a portion of the flow from at least one transducer emitting ultrasonic radiation to at least one transducer receiving ultrasonic radiation to generate a second received signal which propagates partly through the conduit wall and partly through the fluid; and (d) providing for the signal processing arrangement to determine from the first and second signals ultrasonic radiation propagation time periods through the first path and through the at least one second path, and to perform computational operations on the propagation time periods to determine the properties of the flow in respect of at least one of: a flow velocity (v) of the fluid in the conduit, a velocity of sound (c) through the fluid.

Optionally, the method is implemented such that computation of the flow velocity (v) of the fluid and/or the velocity (c) of sound in the fluid from the propagation time periods is executed in combination with utilizing data relating to phase velocity of Lamb waves in the one or more walls of the conduit and a spatial dimension (D) of the conduit.

Optionally, the method includes determining the ultrasonic radiation propagation time periods through the first path and through the at least one second path in upstream and downstream directions relative to the flow of fluid.

Optionally, the method includes arranging for the propagation time periods via a plurality of the at least one second path are temporally mutually similar so as to provide the signal processing unit with a single temporal pulse or pulse burst for performing time measurements for determining the fluid flow velocity (v) and/or the velocity of sound (c). More optionally, the method includes arranging for a section of the conduit to have a substantially constant transverse dimension (D) in respect of an axial direction of the conduit in a region between transducers of the transducer arrangement, the constant transverse dimension (D) enabling propagation time delays via the at least one second path to be mutually temporally similar.

Optionally, the method includes arranging for at least one flow restriction to be included in the conduit for generating a pressure difference thereacross in response to fluid flow therethrough, and measuring using pressure sensors a pressure difference developed across the at least one flow restriction and generating a pressure signal ($S_P$) indicative of the pressure difference for a signal processing arrangement, and a temperature sensor arrangement for measuring a temperature of the flow of fluid and/or temperature differences across pipe lengths or pipeline components associated with the conduit for providing the signal processing arrangement with temperature signals ($S_T$) indicative of temperature, and utilizing in the signal processing arrangement any combination of one or more pressure measurements, one or more pressure difference measurements, one or more temperature measurements, one or more temperature difference measurements, a fluid flow velocity and a mixture speed of sound to determine one or more fluid flow rate), one or more fluid fractions, and/or one or more fluid characteristics indicative of viscosity and/or density of the one or more fluids or one or more fluid phases. Determination of viscosity and/or density is useful in measuring multiphase fluid mixtures flowing through the apparatus; for example, when the fluid flow includes a mixture of two fluids, or a fluid with solid particles therein, measurements of pressure, temperature, flow velocity (v) and speed of sound (c) allow a set of simultaneous equations to be solved whose solution provides a ratio of fluids to be computed. Such determination of multiphase mixture is, for example, highly useful in oil production industries wherein mixtures of any combination of typically oil, water, gas, chemicals, sand, need to be monitored for control purposes, for example controlling an instantaneous rate of oil produced from an oil well.

Optionally, the method includes arranging for the transducers arrangement to include a plurality of pairs of transducers for measuring spatially differential fluid flows within the conduit, for example for increasing robustness of measurements for, and/or corrections for:
(a) fluid flow velocity profiles in the conduit; or
(b) spatial phase distributions if more than one fluid phase is present in the conduit.

Optionally, the method includes measuring attenuation of the ultrasonic signal following the first path to provide input to a frequency tuning algorithm for tuning the signal for achieving an optimal energy transfer into the fluid.

Optionally, the method includes using the attenuation measurement as a first measure on the fluid density, based upon an attenuation of certain guided wave modes being mainly proportional to an acoustic impedance ratio between the fluid and the conduit.

Optionally, the method includes arranging the transducer arrangement and the signal processing arrangement to excite wave modes with essentially tangential motion on the surface of the one or more walls, wherein the wave modes are of a nature to couple into the fluid in the conduit as a function of a viscosity of the fluid, and measuring attenuation of these wave modes in the one or more walls for computing a viscosity of the fluid within the conduit.

According to a third aspect of the invention, there is provided a software product recorded on a machine-readable data carrier, wherein the software product is executable on computing hardware for executing a method pursuant to the second aspect of the invention.

Features of the invention are susceptible to being combined in any combination without departing from the scope of the invention as defined by the claims.

DESCRIPTION OF THE DIAGRAMS

Embodiments of the invention will now be described, by way of example only, with reference to the following diagrams wherein:

FIG. 4 is a schematic illustration of signal propagation within a conduit is association with the apparatus of FIG. 3;

FIG. 8 is an example of a more advanced version of the apparatus if FIG. 3 adapted for measuring fluid flow velocity v, speed of sound velocity c and viscosity of a fluid flow within a conduit.

DESCRIPTION OF EMBODIMENTS OF THE INVENTION

Figure 2:
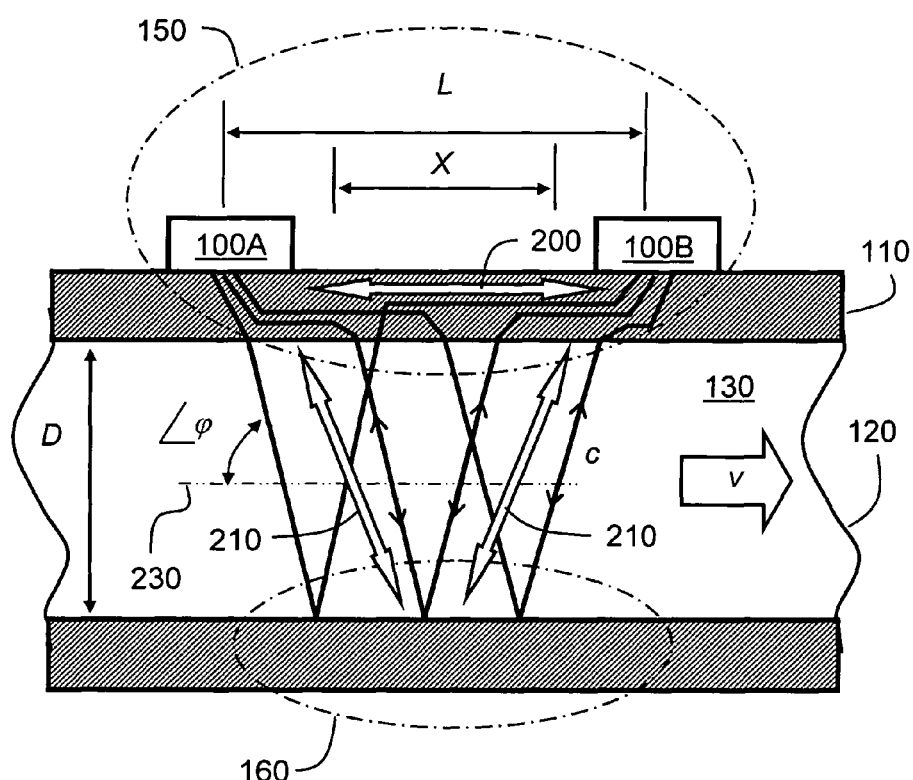
FIG. 2 is a schematic diagram of a transducer arrangement for a flow measuring apparatus pursuant to the present invention.

Flow measuring apparatus pursuant to the present invention employs at least two transducers 100A, 100B which are mounted onto an outer surface of a wall 110 of a conduit 120 which guides a flow of a fluid 130 when in operation. The transducers 100A, 100B are spatially mounted with a distance L between them in an axial direction of the conduit 120 as illustrated in FIG. 2. The transducers 100A, 100B are mounted onto a first portion 150 of the wall 110 as illustrated. Moreover, a second portion 160 of the wall 110 is opposite and parallel to the first portion 150 of the wall 110 as illustrated. The second portion 160 of the wall 110 is operable to reflect acoustic energy from the fluid 130 on account of the conduit 120 having a suitable, e.g. circular or rectangular profile. Beneficially, the conduit 120 is circular and has a substantially constant diameter in a region between the transducers 100A, 100B at the first and second portions 150, 160. Ultrasonic radiation transmitted and/or received at the conduit wall 110 through the mechanism of Lamb wave propagation subtends an angle $\phi$ as shown. The present invention is clearly distinguished from the aforementioned conventional flow measuring apparatus in that selection of the distance L between the transducers 100A, 100B is de-coupled from selection of the angle $\phi$ of acoustic radiation propagating into the flow of fluid 130 in the conduit 120. Such de-coupling has an important benefit that ultrasonic radiation propagation time $t_{fluid}$ within the fluid 130 is independent of flow velocity within the fluid 130. Moreover, there is a further benefit provided by the present invention in that uncertainties due to flow-dependent propagation paths are alleviated, thereby addressing a fundamental problem encountered in conventional ultrasonic flow measuring apparatus.

In overview, the measuring apparatus illustrated in FIG. 2 employs a first transducer of the transducers 100A, 100B to stimulate Lamb modes that propagate in the wall 110 of the conduit 120. A portion of the stimulated Lamb modes propagating within the wall 110 will radiate into the fluid 130 in a spatially distributed manner at an angle $\phi$, namely in a different manner in comparison to a point source radiation coupling to fluid as occurs in conventional ultrasonic flow measuring apparatus. The angle $\phi$ is determined by the phase velocity $c_p$ of the Lamb mode and the sound velocity c of the fluid 130. This angle $\phi$ and the sound velocity c determine a time needed for an ultrasonic wave to propagate outwardly across the conduit 120 having a radial dimension D from the first portion 150 of the wall 110, to be reflected off the opposite portion 160 of the wall 110, and to propagate back to the first portion 150 of the wall 110. An axial distance X from the point of radiation of the ultrasonic waves into the fluid 130 to the point whereat the radiation re-enters the wall 110 after propagation in the fluid 130 is determined by the radial dimension D, the angle $\phi$, the sound velocity c and the flow velocity v. A portion of the ultrasonic waves reflected back and impinging on the wall 110 will stimulate Lamb waves in the wall 110, the stimulated Lamb waves being of a similar nature to Lamb waves generated to excite the fluid 130. A receiving transducer amongst the transducers 100A, 100B will detect several signals resulting from:
(a) a first path 200 pertaining to direct Lamb wave propagation in the wall 110 from a sending transducer of the transducers 100A, 100B to a receiving transducer of the transducers 100A, 100B, and (b) a second path 210 pertaining to Lamb wave propagation in the wall 110 coupling into the fluid 130 to generate ultrasonic waves propagating in the fluid 130, the ultrasonic waves in the fluid 130 being reflected from an opposite wall of the conduit 120, with reflected radiation propagating back to the wall 110 to couple via Lamb waves into the wall 112 to be eventually received at a receiving transducer of the transducers 100A, 100B.

These several signals will thus be due to direct propagation along the wall 110 and indirect propagation sequentially through both the wall 110 and the fluid 130. Ultrasonic waves propagating via the second path 210 results in Lamb wave coupling from the wall 110 to the fluid 130 over a continuous section of the conduit 120 giving rise to an infinite number of ultrasonic radiation raylets propagating along their associated paths which are conveniently visualized as a radiating field in contradistinction to conventional systems for ultrasonic flow measurement which assume a single simple ray path for ultrasonic radiation propagating through transducer portions, conduit walls, and a fluid, being refracted according to Snell's Law at all boundary interfaces.

The present invention is distinguished from conventional fluid flow measuring devices in that a flow measuring apparatus pursuant to the present invention is operable to measure a distance X covered by a point of stationary phase within a field wave as described above. The distance X is directly associated with the fluid flow velocity v and is not affected by the same sources of uncertainty as arise in conventional fluid flow measuring apparatus. Beneficially, the distance X is measured by comparing the transit times of signals propagating along the first path 200 in relation to signals propagating along the second path 210 for upstream and downstream measurements made in respect of fluid flow within the conduit 120. Beneficially, the sound velocity c in the fluid 130 can also be computed from the transit times, namely the same four transit times as will be described in more detail later. Thus, the present invention provides an advantage that a minimum of only two transducers are needed for accurately measuring both flow velocity v and sound velocity c in the fluid 130 flowing in the conduit 120. Optionally, additional transducers can be utilized to extract additional information, for example spatial flow profile within the conduit 120 as will be described in more detail later.

A theoretical basis for implementing embodiments of the present invention will now be described. Consider a flow measuring apparatus as illustrated in FIG. 2 with its pair of transducers 100A, 100B mounted onto an outside surface of the wall 110 of the conduit 120. The transducers 100A, 100B alternate between transmitting and receiving ultrasonic signals so that both upstream and downstream measurements are implemented. A transmitting transducer of the transducers 100A,100B excites a Lamb guided-wave mode in the wall 110 of the conduit 120 of which a portion spatially progressively couples into the fluid flow within a volume defined by the walls 110 to generate radiated radiation within the fluid 130. The radiation subtends an angle φ as defined by Snell's law and expressed in Equation 2 (Eq. 2):

$$c = c_p \cos \phi \qquad \text{Eq. 2}$$

wherein c is the sound velocity in the fluid 130 and $c_p$ is the phase velocity of the Lamb mode, and φ is the angle between the direction of sound propagation in the fluid 130 and the axis 230 of the conduit 120. Velocity components in axial and radial directions for the ultrasonic signal in the fluid 130 are given by Equations 3 and 4, respectively (Eq. 3 & Eq. 4):

$$c_x = c \cos \phi \qquad \text{Eq. 3}$$

$$c_y = c \sin \phi \qquad \text{Eq. 4}$$

wherein y-axis defines a radial direction and x-axis defines an axial direction parallel to the axis 230.

The time needed for an acoustic signal to travel twice across the conduit 120 in association with a reflection at the second portion 160 of the wall 110, namely to travel a distance 2D, is defined by Equation 5 (Eq. 5):

$$t_{fluid} = \frac{2D}{c_y} = \frac{2D}{c_p \sin\varphi \cos\varphi} \qquad \text{Eq. 5}$$

When the fluid 130 is at rest in the conduit 120, the axial distance traveled by an ultrasonic wave from its point of radiation from the first portion 150 of the wall 110 into the fluid 130 to its point of re-entry into the first portion 150 of the wall 110 is defined by $X_0$ as defined in Equation 6 (Eq. 6):

$$X_0 = t_{fluid} c_x = t_{fluid} c \cos\varphi = \frac{2D}{\tan\varphi} \qquad \text{Eq. 6}$$

If the fluid 130 is in motion with a uniform axial flow velocity of magnitude v, the axial component of the acoustic propagation velocity is modified by convection, so that the distance covered during acoustic propagation in the fluid is defined by Equation 7 (Eq. 7):

$$X_{up}^{dn} = t_{fluid}(c_x \pm v) = \frac{2D}{\tan\varphi} \pm \frac{2Dv}{c_p \sin\varphi \cos\varphi} \qquad \text{Eq. 7}$$

wherein "dn" and "up" refer to downstream and upstream sound propagation directions through the fluid 130 respectively. The contribution to X due to flow of the fluid 130 is positive for the downstream propagation of the sound waves, and negative for the upstream propagation of the sound waves. Equation 7 (Eq. 7) pertains to a single raylet construct in the fluid 130 of the conduit 120. Provided that there is a constant transverse dimension D of the conduit 120 within the area of the portions 150, 160 of the conduit walls, all such raylets will combine constructively to form a single signal arriving at a receiving transducer amongst the transducers 100A, 100B. The example herein pertains to uniform flow, but any essentially laminar flow v(y) can be treated similarly by integration, or summation corresponding to sub-domains, along the raylet paths. The propagation time $t_{fluid}$ depends on the radial sound velocity component only and thus remains constant when the flow velocity of the fluid 130 is on average in the axial direction along the conduit 120. From Equations 6 and 7, it is possible to determine analytically that a mean value of the upstream and downstream axial propagation distances is equal to the propagation distance $X_0$ when the fluid 130 is at rest as provided in Equation 8 (Eq. 8):

$$\hat{X} = \frac{1}{2}(X_{dn} + X_{up}) = \frac{2D}{\tan\varphi} = X_0 \qquad \text{Eq. 8}$$

Whereas a corresponding relationship to Equation 8 (Eq, 8) for upstream and downstream distances in convention fluid flow measuring apparatus holds only as an approximation when $v^2 \ll c^2$, Equation 8 (Eq. 8) pertains for all magnitudes of velocities v and c.

In respect of the present invention, the difference between the axial propagation distances $X_{dn}$ and $X_{up}$ can be measured by comparing the upstream and downstream times-of-flight through the first and second paths 200, 210; as aforementioned, the first path 200 refers to guided-wave propagation within the wall 110 of the conduit 120 along the distance L, and the second path 210 refers to guided-wave propagation over a distance $(L-X_{up}^{dn})$ in addition to propagation through the fluid 130 and one reflection on the second portion 160 of the wall 110. For measuring the flow rate of the fluid 130, a total of four measurements are made, namely one for each of the two paths 200, 210 for upstream and downstream directions as provided in Equations 9 and 10 (Eq. 9 & Eq. 10) wherein "path1" and "path2" correspond to the paths 200, 210 respectively:

$$t_{path1_{up}}^{dn} = t_{delay_{up}}^{dn} + t_{pipe}(L) \quad \text{Eq. 9}$$

$$t_{path2_{up}}^{dn} = t_{delay_{up}}^{dn} + t_{fluid_{up}}^{dn} + t_{pipe}(L - X_{up}^{dn}) \quad \text{Eq. 10}$$

wherein $t_{delay}$ is a system delay of electronics and ultrasonic transducers. In general, a guided-wave propagation time of a point of stationary phase on the surface of the conduit 120 corresponding to a propagation length $\Delta x$ is given by Equation 11 (Eq. 11):

$$t_{pipe}(\Delta x) = \frac{\Delta x}{c_p} \quad \text{Eq. 11}$$

The aforementioned four time measurements can be combined as provided in Equation 12 (Eq. 12):

$$t_{path2,dn} + t_{path2,up} - t_{path1,dn} - t_{path2,up} = \quad \text{Eq. 12}$$
$$t_{delay,dn} + t_{fluid,dn} + t_{pipe}(2L - X_{dn} - X_{up}) +$$
$$t_{delay,up} + t_{fluid,up} - t_{deay,dn} - 2t_{pipe}(L) - t_{delay,up} =$$
$$t_{fluid,dn} + t_{fluid,up} + t_{pipe}(X_{dn} - X_{up}) = 2(t_{fluid} - t_{pipe}(\hat{X}))$$

From Equation 12, it is possible by inserting an expression defining the angle φ as a function of the time measurements, given the phase velocity $c_p$ and the distance D to yield Equation 13 (Eq. 13):

$$t_{path2,dn} + t_{path2,up} - t_{path1,dn} - t_{path1,up} = 2(t_{fluid} - t_{pipe}(\hat{X})) \quad \text{Eq. 13}$$
$$= 2t_{fluid}(1 - \cos^2\varphi)$$
$$= 2t_{fluid}\sin^2\varphi$$
$$= \frac{4D}{c_p}\tan\varphi$$

The time measurement of Equations 9 and 10 can be combined to yield an expression Equation 14 (Eq. 14) relating time measurement to the fluid 130 velocity v, the angle φ and the phase velocity $c_p$ of Lamb waves in the wall 110:

$$t_{path2_{up}}^{dn} - t_{path1_{up}}^{dn} = t_{delay_{up}}^{dn} + t_{fluid} + t_{pipe}(L - X_{up}^{dn}) - \quad \text{Eq. 14}$$

-continued
$$t_{delay_{up}}^{dn} - t_{pipe}(L)$$
$$= t_{fluid} - t_{pipe}(X_{up}^{dn})$$
$$= t_{fluid} - \frac{X_{up}^{dn}}{c_p}$$
$$= 2\frac{D}{c_p \sin\varphi\cos\varphi} - \frac{2D}{c_p}\frac{c_p\cos^2\varphi \pm v}{c_p\sin\varphi\cos\varphi}$$
$$= \frac{2D}{c_p\sin\varphi\cos\varphi}\left(1 - \cos^2\varphi - \frac{\pm v}{c_p}\right)$$

Equation 14 is susceptible to being reorganized to provide Equation 15 (Eq. 15):

$$v = \frac{c_p^2 \sin\varphi\cos\varphi}{4D}(t_{path2,up} - t_{path2,dn} - t_{path1,up} + t_{path1,dn}) \quad \text{Eq. 15}$$

In practice, it is feasible to measure the phase velocity $c_p$ for Lamb waves propagating along the wall 110 of the conduit 120 along the first path 200 (path1) as defined by Equation 16 (Eq-16):

$$c_p = \frac{L}{t_{path1_{up}}^{dn} - t_{delay_{up}}^{dn}} \quad \text{Eq. 16}$$

From Equation 16, the sound velocity c in the fluid 130 is susceptible to being computed by a direct use of Snell's law as in Equation 17 (Eq. 17):

$$c = c_p \cos\varphi \quad \text{Eq. 17}$$

wherein $$\varphi = \arctan\left(\frac{c_p}{4D}(t_{path2,dn} + t_{path2,up} - t_{path1,dn} - t_{path1,up})\right) \quad \text{Eq. 18}$$

Thus, in a flow measuring instrument, four transit time measurements are made along the first and second paths (path1, path2) 200, 210 respectively in upstream and downstream directions. These four time measurements are combined to enable the flow velocity v to be computed using Equation 15 and the velocity of sound c is computed using Equations 17 and 18 (Eq. 17 and Eq. 18).

Figure 3:
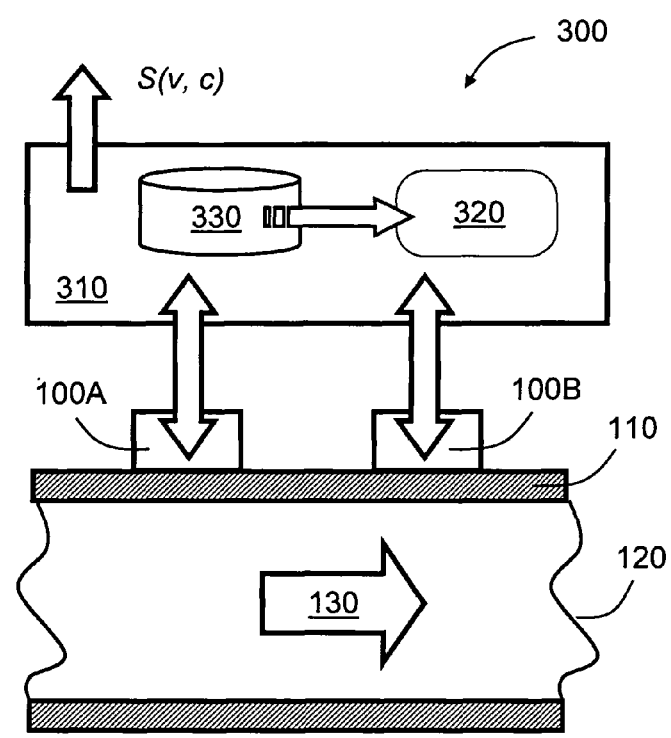
FIG. 3 is a schematic diagram of an embodiment of a flow measuring apparatus pursuant to the present invention.

An embodiment of a flow measuring apparatus pursuant to the present invention is illustrated in FIG. 3. In FIG. 3, the flow measuring apparatus is indicated generally by 300 and includes at least the two transducers 100A, 100B, and a signal processing unit 310 comprising a data processing unit 320 coupled to data memory 330. Software products are stored in the data memory 330 implemented as machine readable data medium, the data memory 330 being coupled in data communication with the data processing unit 320.

In operation, the apparatus 300 is operable to excite one or more of the transducers 100A,100B to inject ultrasonic radiation into the flow 130 in the conduit 120. Moreover, the apparatus 300 is concurrently operable to receive signals from the transducers 100A, 100B for processing. The aforementioned software products are operable to control operation of the apparatus 300 when executed on the signal processing unit 310. In addition, the apparatus 300 includes an output whereat a signal S(v, c) is provided, for example as a data stream, the signal S(v, c) including a measure of fluid velocity v and/or speed of sound c within the fluid 130 included within the conduit 120. Optionally, the conduit 120 is an integrated part of the apparatus 300. Alternatively, the apparatus 300 can be implemented so that it can be retrofitted to existing installed conduits. Other installation possibilities are also feasible.

As mentioned elsewhere in relation to the present invention, the signal processing unit 310 is optionally deployed at a same locality as the transducers 100A, 100B. Alternatively, the signal processing unit 310 is disposed remotely from the transducers 100A, 100B, for example for enabling the transducers 100A, 100B to be employed in high-temperature environments which would be excessive for data processing hardware based upon silicon microfabricated devices. Optionally, the transducers 100A, 100B are provided with local electronic components which are capable of operating at elevated temperatures, for example miniature thermionic in-situ driver amplifiers for exciting the transducers 100A, 100B and for amplifying received signals generated by the transducers 100A, 100B in response to receive ultrasonic radiation.

Signals generated by the signal processing unit 310 to stimulate the transducers 100A, 100B to generate ultrasonic radiation within the conduit 120 comprise a series of bursts of pulses as illustrated schematically in FIG. 4 with reference to a horizontal time line. Each burst of pulses is repeated at a time interval T1 which is beneficially longer than a propagation time for the radiation to propagate from a first of the transducers 100A, 100B via the second path 210 (path2) to reach a second of the transducers 100A, 100B. Moreover, a duration of the burst of pulses T2 is beneficially shorter than a period of time required for ultrasonic radiation to propagate via the first path (path1) 200 as Lamb waves from a first of the transducers 100A, 100B to a second of the transducers 100A, 100B. A period of each pulse T3 is beneficially less than the duration of the burst of pulses T2; for example, each burst of pulses beneficially includes in a range to 2 to 20 pulses.

Referring to FIG. 4, each transducer 100A, 100B optionally includes a piezo-electric element 350 which is optionally coupled via a wedge-like element 360 to an exterior surface of the wall 110 for selectively exciting one or more specific guided-wave modes in the one or more conduit walls 110, and hence an improved signal-to-noise ratio for a given magnitude of drive signal generated by the signal processing unit 310. Alternatively, electro-magnetic devices and/or electrostatic devices are utilized for implementing the transducers 100A, 100B. When the transducer 100A is stimulated by a drive signal from the signal processing unit 310, ultrasonic radiation experiences a first time delay $t_1$ propagating through the transducer 100 and electronics and optionally a wedge element 360, a second time delay $t_2$ propagating as Lamb-waves within the wall 110, a third time delay $t_3$ propagating as an outgoing wave in the fluid 130, a fourth time delay $t_4$ propagating as a reflected wave, a fifth time delay $t_5$ propagating as a re-entered Lamb wave in the wall 110, and a sixth time delay $t_6$ propagating through the optional wedge-like element 360 and the transducer 100B, and receiving electronics. Thus, the total propagation time $t_t$ for the ultrasonic radiation to propagate from the optionally piezo-electric element 360 of the first transducer 100A to the optionally piezo-electric element 360 of the second transducer 100B is given by Equation 19 (Eq. 19):

$$t_t = t_1 + t_2 + t_3 + t_4 + t_5 + t_6 \qquad \text{Eq. 19}$$

Equation 19 also pertains to ultrasonic radiation propagating from the second transducer 100B to the first transducer 100A. Flow within the fluid 130 influences the total time $t_t$.

Figure 1:
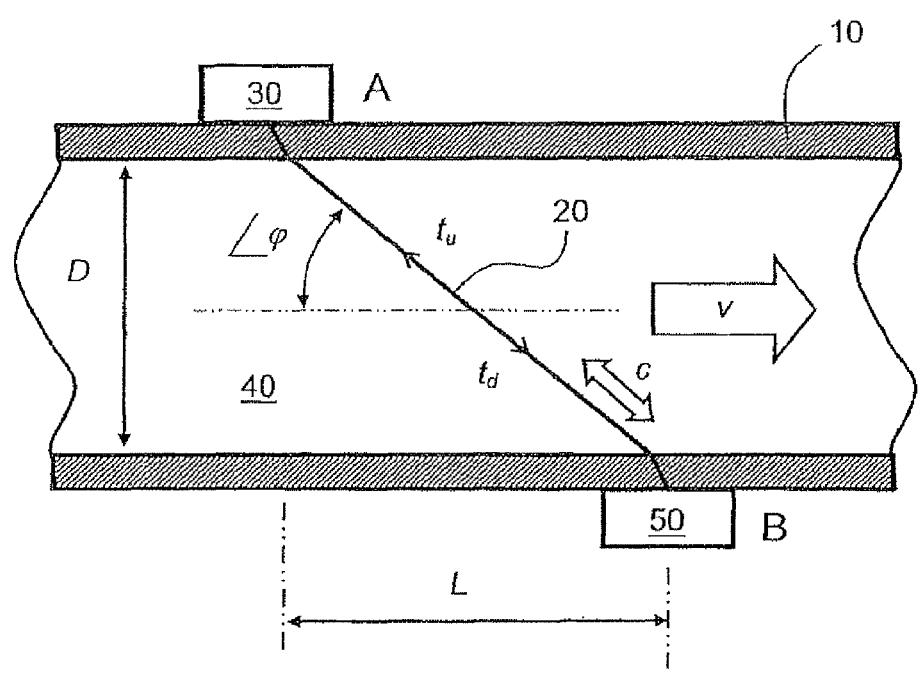
FIG. 1 is a schematic diagram of ultrasonic signal propagation within a conventional ultrasonic flow measuring apparatus.
Figure 5:
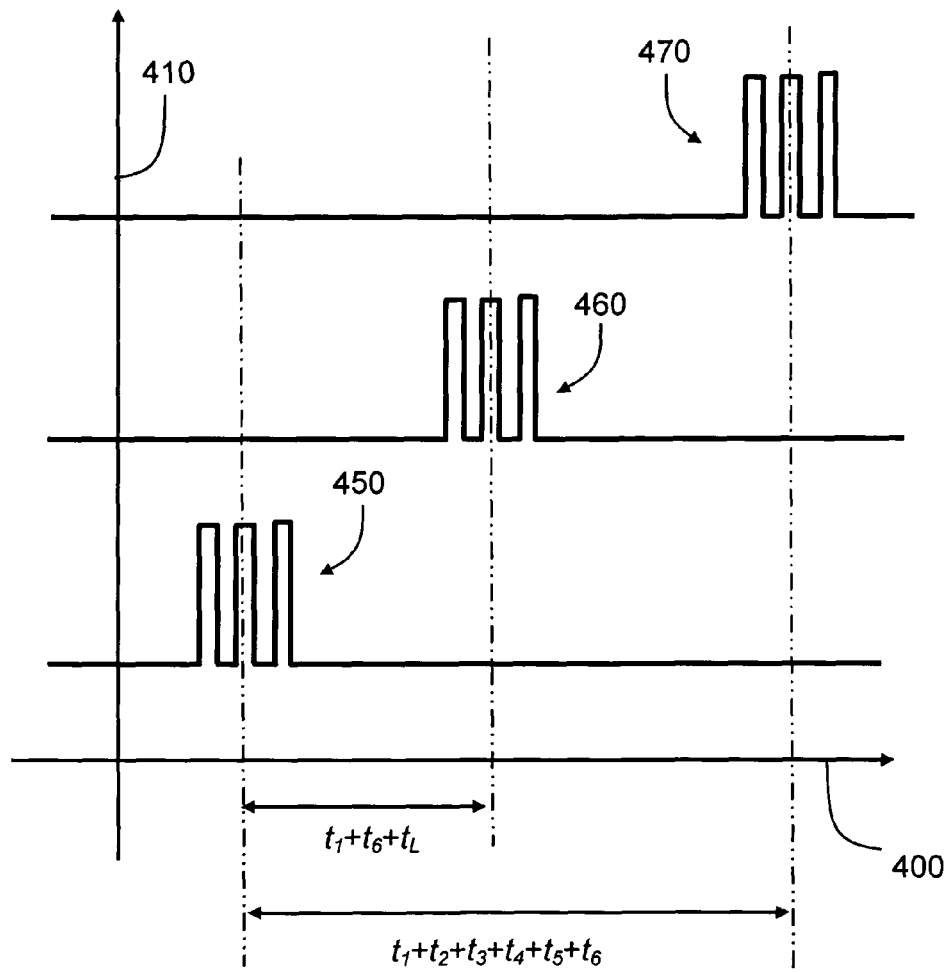
FIG. 5 is a schematic example of measurement signal obtained during operation of the apparatus of FIG. 3.

Conventional flow measuring apparatus, for example as illustrated in FIG. 1, attempt to measure a total propagation time, namely equivalent to $t_t$ in Equation 19, for determining the fluid flow velocity v and the speed of sound c within the fluid 130. Such a conventional approach results in measurement inaccuracies which the fluid flow measuring apparatus operating pursuant to the present invention avoids. Flow measuring apparatus pursuant to the present invention is distinguished from conventional ultrasonic flow measuring apparatus in that the pulse of ultrasonic radiation propagating as Lamb waves along the first path 200 (path1) from one of the transducers 100A, 100B to the other thereof is used as a time reference for measuring a time of propagation of the same pulse of radiation propagating along the second path 210 (path2). Such temporal relationship of the pulse as it propagates along the first and second paths 200, 210 is illustrated in FIG. 5. However, for measuring the phase velocity $c_p$, it is necessary to determine the time delays $t_1$ and $t_6$.

In FIG. 5, an abscissa time axis is denoted 400 with increasing time from left to right, and an ordinate axis 410 denotes signal strength of the pulse burst in the received signal increasing from bottom to top for each of the three sub-plots. A first pulse burst indicated by 450 is applied to a transmitter transducer amongst the transducers 100A, 100B. A pulse burst indicated by 460 is received at a receiver transducer amongst the transducers 100A, 100B resulting from Lamb wave propagation solely along the first path 200 (path1). A time $t_L = t_{pipe}(L)$ is used to denote a time for Lamb waves to propagate along a distance L as aforementioned. A pulse burst indicated by 470 is received at the receiver transducer as a result of the ultrasonic radiation excited by the burst of pulses propagating along the second path 210 (path2); this second path 210, as aforementioned, includes multiple raylets having mutually similar propagation time delays. A time difference $\Delta t$ between receiving the pulse bursts 460, 470 is given by Equation 20 (Eq. 20):

$$\Delta t = (t_2 + t_5 - t_L) + (t_3 + t_4) \qquad \text{Eq. 20}$$

In Equation 20, expressions in the left-hand bracket are defined by Lamb wave propagation within the wall 110 of the conduit 120 affected by the flow 130 in the fluid by way of the distance X being modified, whereas expressions in the right-hand bracket represent the propagation time in the fluid, which is not affected by the flow in the fluid. Equation 20 is beneficially computed in the apparatus 300 for upstream and downstream directions in respect of the flow. As shown earlier in Equations 15 to 18, Equation 20 right-hand bracket can be related to the phase velocity $c_p$ of the lamb wave in the wall 110 and to the dimension D to provide a highly accurate computation of fluid flow velocity v as well as speed of sound c within the fluid 130. This improved description of the propagation delays facilitates use of Lamb waves in an ultrasonic flow meter by avoiding the assumption of sound propagation along a fixed path.

The transducers 100A, 100B in combination with the conduit 120 and the design of the pulse bursts are suitably shaped so that the pulse bursts 460, 470 when received at the receiving transducer are temporally well defined and temporally compact. Such a characteristic is achieved by ensuring that all raylets, as illustrated in FIG. 2 and FIG. 4, being excited by Lamb waves coupling from the wall 110 to the fluid 130 and vice versa, have a mutually similar value for a sum of the times $(t_3 + t_4)$. For example, it is beneficially that the conduit 120 has a constant nominal diameter for its dimension D and a constant wall 110 thickness over a region between the transducers 100A, 100B, for example within less than a, threshold variation in dimensions along this length between the transducers 100A, 100B. Optionally, the threshold variation is less than 10%, more preferably less than 3%, and most preferably less than 1%. The signal processing unit 320 beneficially has a high-precision timing clock associated therewith, for example based upon a quartz crystal resonator, for accurately measuring times of the pulses 450, 460, 470 for upstream and downstream directions for generating parameters for use in computations represented by Equations 15 to 18 (Eq. 15 to Eq. 18) executed within the signal processing unit 320 for computing fluid flow velocity v and/or velocity of sound c within the fluid 130. The present invention is thus a considerable advance in comparison to conventional approaches on account of contributions from various error sources having been removed.

Figure 6:
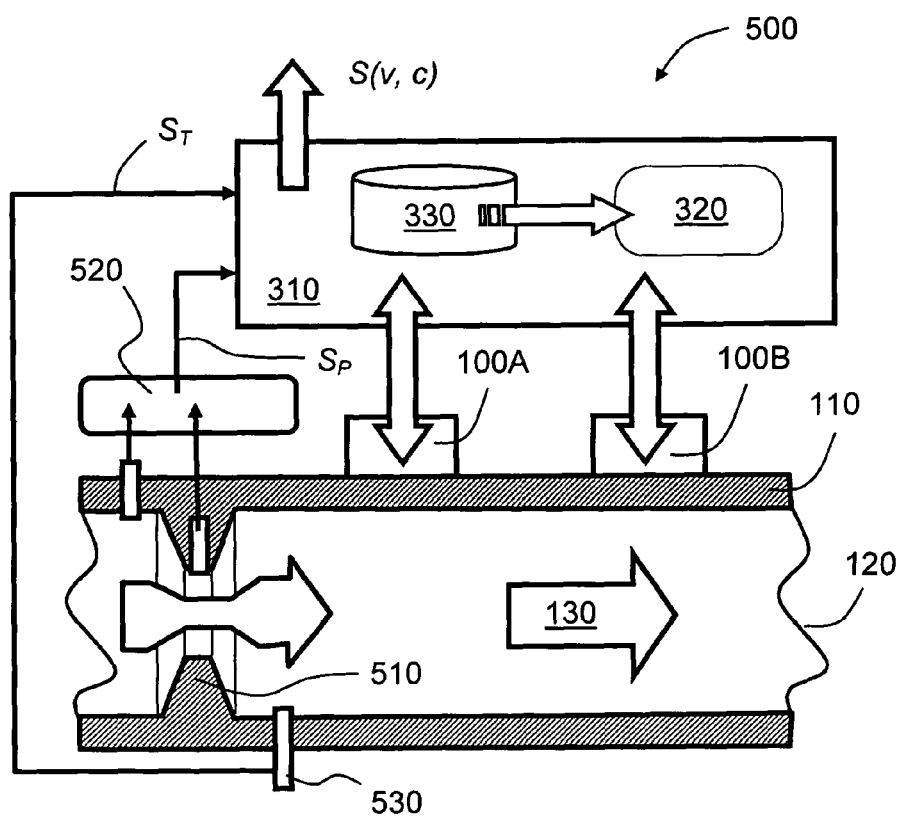
FIG. 6 is an example of a more advanced version of the apparatus of FIG. 3.

The apparatus 300 is susceptible to being further evolved, for example to generate a flow measuring apparatus indicated generally by 500 in FIG. 6, wherein the conduit 120 is provided with a flow restriction 510, for example a Venturi flow restriction, for generating a pressure differential thereacross in response to a flow of a fluid 130 therethrough, which is sensed by a pressure sensor 520 whose pressure indicative output signal $S_P$ is coupled to the signal processing unit 310. Optionally, the flow restriction 510 is implemented in the form of an actuated valve for controlling fluid flow, for example a valve operable to switch a direction of fluid flow between a plurality of different conduits in an subterranean network of boreholes associated with oil exploration, carbon dioxide capture and storage. Optionally, one transducer of the pressure sensor 520 is mounted before the restriction 510 and another transducer of the pressure sensor 520 is mounted on the restriction 510 as illustrated, although other placements of the transducers of the pressure sensor 520 are feasible. The Venturi flow restriction 510 is beneficially also equipped with a temperature sensor 530 for measuring a temperature of the flow of the fluid 130, wherein a temperature indicative signal $S_T$ is also provided to the signal processing unit 310. Measurement of the flow velocity v using Equations 15 to 18, the temperature $S_T$ of the fluid 130 and the pressure difference $S_P$ enables a viscosity of the fluid 130 and/or the density of the fluid 130 to be computed and thereby insight obtained regarding a nature of the composition of the fluid 130, for example determining of its constituent parts when the fluid 130 is a multiphase mixture.

Optionally, the signal processing unit 310 is operable to monitor the temporal form of the pulse bursts 460, 470 and adjust one or more of the periods T2 and T3 for obtaining an optimal temporal form for the pulse bursts 460, 470 for proving a most accurate determination of pulse times for utilizing in Equations 15 to 18 when executed in the data processing unit 320. Such adjustment of T2 and T3 can be performed rapidly by an iterative algorithm for a situation in which the flow of fluid 130 in the conduit 120 is quasi-constant. Such adjustment may include, but is not limited to, frequency adjusting the pulse burst 450.

Figure 7:
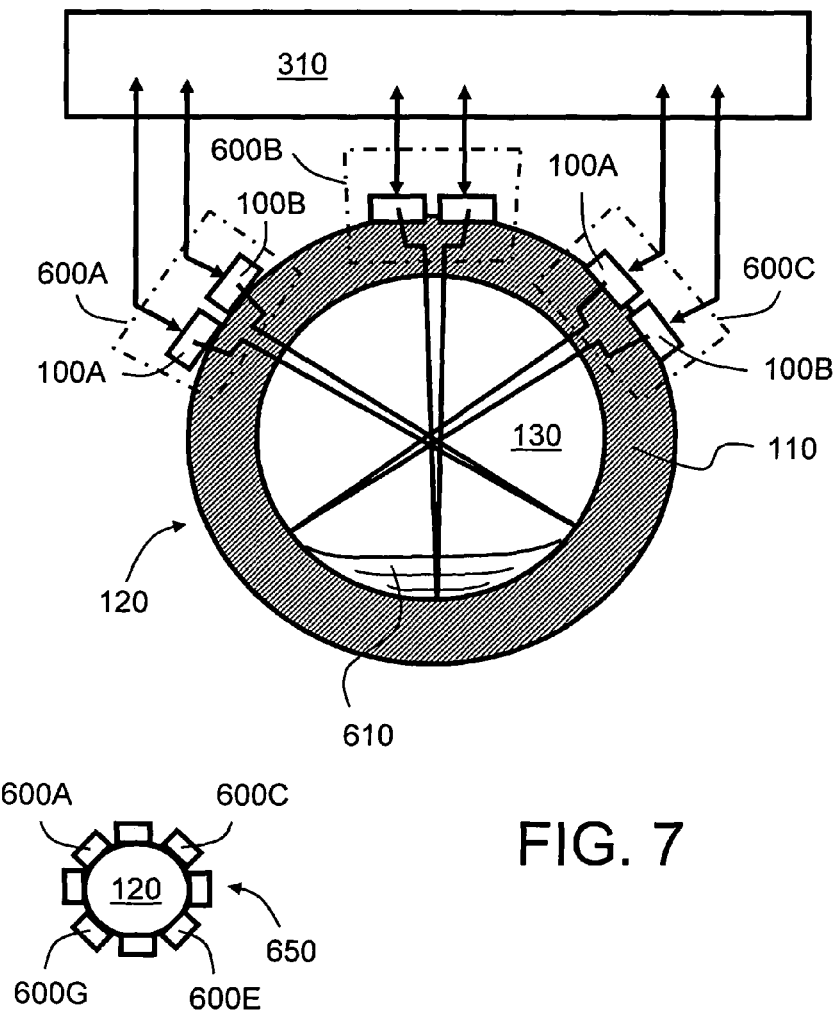
FIG. 7 is a example of a more advanced version of the apparatus of FIG. 3 adapted for measuring spatial variations of fluid flow velocity and sound velocity within a conduit.

In FIG. 7, there is shown an optional embodiment of a flow measuring apparatus pursuant to the present invention for measuring spatially differential flows within the conduit 120. The walls 110 of the conduit 120 are beneficially implemented to have a substantially circular profile as illustrated in cross-section. Pairs of transducers 100A, 100B are disposed along and around the walls 110 of the conduit 120 so that the second paths 210 for each set 600A, 600B, 600C of transducers 100A, 100B intersect the fluid 130 at different angles. The sets of transducers 600A, 600B, 600C are coupled to the signal processing unit 310. Moreover, the signal processing unit 310 is arranged to service the sets of transducers 600A, 600B, 600C rapidly in sequence, for example in a multiplexed manner, or simultaneously in a substantially concurrent manner. For a substantially spatially uniform flow of fluid 130 within the conduit 120, the sets of transducers 600A, 600B, 660C in cooperation with their signal processing unit 310 generate substantially similar signals. However, when the flow of fluid 130 is non-uniform, for example a layer of sand sediment 610 is flowing more slowly at a bottom region of the conduit 120 otherwise filled with for example oil and water, signals generated by utilizing the sets of transducers 600A, 600B, 600C will be mutually different; such difference can be utilized by the signal processing unit 310 to characterize a non-uniform nature of flow in the conduit 120. Optionally, the conduit 120 can be furnished with pairs of transducers 100A, 100B around its circumference, for example the pairs 600 being implemented at 72° intervals. The transducers 100A, 100B of the sets of transducers 600A, 600B, 600C are disposed along the conduit 120 in a manner as depicted in FIG. 2 and FIG. 4.

Optionally, the apparatus 300, 500 is implemented such that sound signal attenuation of the first path 200 can be monitored to provide an input to a frequency tuning algorithm for adjusting operation of the apparatus 300, 500 for obtaining optimal energy transfer into the fluid 130. Optionally, a measurement of the attenuation is used as a first measure of the fluid density, based upon the attenuation of a preferred density-sensitive mode being mainly proportional to an acoustic impedance ratio between the fluid and the conduit.

As a further modification to the apparatus 300, 500, it is optionally feasible to use the transducers 100A, 100B in a suitably modified form, for example by including a plurality of additional elements therein, suitable for exciting guided-wave modes with predominantly tangential motion on the surface of the conduit wall 110 between the transducers 100A, 100B. Such shear motion couples significantly from the wall 110 between the transducers 100A, 100B to the fluid 130 as a function of viscosity of the fluid 130 and thus enables calculation of fluid viscosity based on measurements of attenuation of the guided mode. Referring to FIG. 8, there is a shown an illustration of a first modified from of the apparatus 300 in FIG. 3; the first modified apparatus in FIG. 8 is indicated generally by 700. The apparatus 700 includes integrated into housings of the transducers 100A, 100B additional transducers 710A, 710B for generating and/or receiving guided waves 720 propagating within the one or more walls 110 and partially coupling to the fluid 130 within the conduit 120 in a manner which is influenced by the viscosity of the fluid 130; component γ is used to denoted density or viscosity. The apparatus 700 is of benefit in that a spatial collocation of the transducers 100A, 710A, similarly the transducers 110B, 710B, together in a same housing with associated connecting cables enables greater functionality to be achieved for a given physical size of apparatus. A second modified version of the apparatus 300 of FIG. 3 is also illustrated in FIG. 8 and indicated generally by 800. The modified apparatus 800 has its transducers 100A, 100B and 710B, 710B spatially mutually separate along the conduit 120. Optionally, in the apparatus, the transducers 710A, 710B are on a section of conduit 120 which can be used as a stand-alone viscosity measuring apparatus, namely independently of the transducer 100A, 100B used for flow velocity v and speed of sound c measurements.

Use of the apparatus 300, 700, 800 in measuring multiphase flows will now be elucidated in greater detail.

Situation 1: a single-phase fluid 130 flows within the conduit 120. The apparatus 300 measures the flow velocity v for the single-phase fluid. The speed of sound c in the single-phase fluid 130 will remain constant for a given temperature of the fluid 130.

Situation 2: a 2-phase fluid 130 mixture flows within the conduit 120. The apparatus 300 measures the flow velocity v and the speed of sound c in the flow. The speed of sound c varies between $c_1$ and $c_2$ according to a proportion of the first and second phases present in the flow, wherein $c_1$ is the speed of sound in the first phase of proportion $\phi_1$, and $c_2$ is the speed of sound in the second phase of proportion $\phi_2$, such that pursuant to Equation 21 (Eq. 21):

$$c = \phi_1 c_1 + \phi_2 c_2,$$

$$1 = \phi_1 + \phi_2 \qquad \text{Eq. 21}$$

Equation 21 is solved in operation in the data processing unit 310.

Situation 3: a 3-phase fluid 130 mixture flows within the conduit 120. The apparatus 600, 700, 800 measures the flow velocity v, the speed of sound c and the density or viscosity γ, such that pursuant to Equation 22 (Eq. 22):

$$c = \phi_1 c_1 + \phi_2 c_2 + \phi_3 c_3,$$

$$1 = \phi_1 + \phi_2 + \phi_3,$$

$$\gamma = \phi_1 \gamma_1 + \phi_2 \gamma_2 + \phi_3 \gamma_3 \qquad \text{Eq. 22}$$

Wherein $\phi_1, \phi_2, \phi_3$ are relative portions of the three phases, $c_1, c_2, c_3$ are speeds of sound in the respective three phases, and $\gamma_1, \gamma_2, \gamma_3$ are viscosities or densities of the respective three phases. Parameters in Equation 22 (Eq. 22) are in practice influenced by temperature and pressure within the conduit 120.

Optionally, one or more additional sensors can be included in the apparatus 500, 700, 800 for sensing the flow of fluid 130 and thereby measuring composition of four or more phases present in the conduit 120. For example, one or more electromagnetic sensors, temperature sensors, electrical resistance sensors can be included in the apparatus 300, 500, 700, 800 to improve measurement performance and functionality. Optionally, temperature and pressure measurements for use in computations in the signal processing unit 310 are obtained from external pressure and/or temperature sensor to the apparatus 300, 500, 700, 800.

As aforementioned, it will be appreciated that the signal processing unit 310 can be optionally disposed remotely from the transducers 100A, 100B, for example for coping with harsh environments where elevated temperatures are encountered, for example down boreholes, in subterranean installations and borehole networks. The present invention is also susceptible to being used in aerospace systems such as fuel supply systems to aircraft and rocket engines, in chemical processing industries such as oil refining, in nuclear reactors, in nuclear waste disposal facilities, in food processing industries, in carbon dioxide capture and storage systems to mention a few possible installations.

Modifications to embodiments of the invention described in the foregoing are possible without departing from the scope of the invention as defined by the accompanying claims.

Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural.

Numerals included within parentheses in the accompanying claims are intended to assist understanding of the claims and should not be construed in any way to limit subject matter claimed by these claims.

The invention claimed is:

1. A flow measuring apparatus (300, 500) for measuring a flow of a fluid (130) within a conduit (120) including one or more walls (110), said apparatus (300, 500) including a transducer arrangement (100A, 100B) including at least one transducer for emitting ultrasonic radiation into the flow (130) and at least one transducer for receiving ultrasonic radiation from the flow (130) in operation, and a signal processing arrangement (310) for generating signals to excite the transducer arrangement (100A, 100B) and for processing received signals provided by the transducer arrangement (100A, 100B) for generating output signals from the signal processing arrangement (310) indicative of properties of the flow, characterized in that said transducer arrangement (100A, 100B) in cooperation with said conduit (120) is operable to provide a first path (200) solely via said one or more walls (110) for Lamb-wave ultrasonic radiation coupling directly from the at least one transducer for emitting ultrasonic radiation to said at least one transducer for receiving ultrasonic radiation to generate a first received signal;

said transducer arrangement (100A, 100B) in cooperation with said conduit (120) is operable to provide at least one second path (210) for propagation of ultrasonic radiation within said one or more walls (100) via Lamb waves coupling to at least a portion of said flow (130) from the at least one transducer for emitting ultrasonic radiation to the at least one transducer for receiving ultrasonic radiation to generate a second received signal; and said signal processing arrangement (310) is operable to determine from said first and second signals ultrasonic radiation propagation time periods through the first path (200) and through the at least one second path (210) in upstream and downstream flow directions, and to perform computational operations on said propagation time periods to determine said properties of the flow in respect of at least one of: a flow velocity (v) of the fluid (130) in the conduit (120), a velocity of sound (c) through the fluid (130).

2. A flow measuring apparatus (300, 500) as claimed in claim 1, wherein said apparatus (300, 500) is operable to compute said flow velocity (v) of said fluid (130) and/or said velocity (c) of sound in said fluid (130) from said propagation time periods in combination with data relating to phase velocity of Lamb waves in said one or more walls (110) of said conduit (120) and a spatial dimension (D) of said conduit (120).

3. A flow measuring apparatus (300, 500) as claimed in claim 1, wherein said propagation time periods via a plurality of said at least one second path (210) are temporally mutually similar so as to provide said signal processing unit (310) with a single temporal pulse (470) or pulse burst (470) for performing time measurements for determining said fluid flow velocity (v) and/or said velocity of sound (c).

4. A flow measuring apparatus (300, 500) as claimed in claim 1, wherein said apparatus (300, 500) is adapted to include and/or be fitted to a section of said conduit (120) having a substantially constant transverse dimension (D) in respect of an axial direction (230) of said conduit (120) in a region between transducers (100A, 100B) of said transducer arrangement (100A, 100B), said constant transverse dimension (D) enabling propagation time delays via said at least one second path (210) to be mutually temporally similar.

5. A flow measuring apparatus (500) as claimed in claim 1, wherein said conduit (120) includes at least one flow restriction (510) for generating a pressure difference thereacross in response to a fluid flow therethrough, and said apparatus (500) includes a pressure sensor (520) for measuring said pressure difference developed across said at least one flow restriction (510) and generating a pressure signal ($S_P$) indicative of said pressure difference for said signal processing arrangement (310), and a temperature sensor arrangement (530) for measuring a temperature and/or temperature difference of said flow of fluid (130) for providing said signal processing arrangement (310) with a temperature signal ($S_T$) indicative of said temperature and/or temperature difference, and said signal processing arrangement (310) is operable to utilize said pressure and/or pressure difference; said temperature and/or said pressure difference and said flow rate of said fluid to determine a viscosity and/or density measurement for said fluid (130).

6. A flow measuring apparatus (300, 500) as claimed in claim 1, wherein said transducers arrangement (100A, 100B) includes a plurality of pairs of transducers (100A, 100B) for measuring spatially differential fluid flows within said conduit (120).

7. A flow measuring apparatus (300,500) as claimed in claim 1, wherein said transducer arrangement (100A, 100B) in cooperation with said signal processing arrangement (310) is operable to excite guided wave modes with predominantly tangential surface motion, said wave modes being of a nature to couple into said fluid (130) as a function of a viscosity of said fluid (130), and wherein said signal processing arrangement (310) is operable to measure attention of said wave modes in said one or more walls (110) for measuring a viscosity of said fluid (130) within said conduit (120).

8. A method of measuring a flow of a fluid (130) within a conduit (120) including one or more walls (110), characterized in that said method includes:
   (a) arranging for a transducer arrangement (100A, 100B) to include at least one transducer for emitting ultrasonic radiation into the flow (130) and at least one transducer for receiving ultrasonic radiation from the flow (130), and arranging for a signal processing arrangement (310) to generate signals to excite the transducer arrangement (100A, 100B) and to process received signals provided by the transducer arrangement (100A, 100B);
   (b) providing for said transducer arrangement (100A, 100B) in cooperation with said conduit (120) to provide a first path (200) solely via said one or more walls (110) for Lamb-wave ultrasonic radiation coupling directly from the at least one transducer for emitting ultrasonic radiation and the at least one transducer for receiving ultrasonic radiation to generate a first received signal;
   (c) providing for said transducer arrangement (100A, 100B) in cooperation with said conduit (120) to provide at least one second path (210) for propagation of ultrasonic radiation within said one or more walls (100) via Lamb waves coupling to at least a portion of said flow (130) from the at least one transducer for emitting ultrasonic radiation to the at least one transducer for receiving ultrasonic radiation to generate a second received signal; and
   (d) providing for said signal processing arrangement (310) to determine from said first and second signals ultrasonic radiation propagation time periods through the first path (200) and through the at least one second path (210) in upstream and downstream flow directions, and to perform computational operations on said propagation time periods to determine said properties of the flow in respect of at least one of: a flow velocity of the fluid (130) in the conduit (120), a velocity of sound through the fluid (130).

9. A method as claimed in claim 8, wherein computation of said flow velocity (v) of said fluid (130) and/or said velocity (c) of sound in said fluid (130) from said propagation time periods is executed in combination with utilizing data relating to phase velocity of Lamb waves in said one or more walls (110) of said conduit (120) and a spatial dimension (D) of said conduit (120).

10. A method as claimed in claim 8, including arranging for said propagation time periods via a plurality of said at least one second path (210) are temporally mutually similar so as to provide said signal processing unit (310) with a single temporal pulse (470) or pulse burst (470) for performing time measurements for determining said fluid flow velocity (v) and/or said velocity of sound (c).

11. A method as claimed in claim 8, including arranging for a section of said conduit (120) to have a substantially constant transverse dimension (D) in respect of an axial direction (230) of said conduit (120) in a region between transducers (100A, 100B) of said transducer arrangement (100A, 100B), said constant transverse dimension (D) enabling propagation time delays via said at least one second path (210) to be mutually temporally similar.

12. A method as claimed in claim 8, including arranging for at least one flow restriction (510) to be included in the conduit (120) for generating a pressure difference thereacross in response to fluid flow therethrough, and measuring using a pressure sensor (520) a pressure difference developed across said at least one flow restriction (510) and/or within said conduit (120) and generating a pressure signal ($S_P$) indicative of said pressure difference and/or said pressure for a signal processing arrangement (310), and a temperature sensor arrangement (530) for measuring a temperature and/or temperature difference of said flow of fluid (130) for providing said signal processing arrangement with a temperature signal ($S_T$) indicative of said temperature and/or temperature difference, and utilizing in said signal processing arrangement (310) said pressure difference, said temperature and said flow rate of said fluid to determine a viscosity and/or density measurement for said fluid (130).

13. A method as claimed in claim 8, including arranging for said transducers arrangement (100A, 100B) to include a plurality of pairs of transducers (100A, 100B) for measuring spatially differential fluid flows within said conduit (120).

14. A software product recorded on a machine-readable data carrier, wherein said software product is executable on computing hardware (320) for executing a method as claimed in claim 8.

15. An apparatus (300, 500, 700) as claimed in claim 1, said apparatus (300, 500, 700) being adapted for performing flow measurements in at least one of:
   (a) down-borehole applications;
   (b) in sub-sea applications;
   (c) in water-injection systems;
   (d) in gas-injection systems;
   (e) in carbon dioxide storage systems;
   (f) in oil and/or gas production;
   (g) in boreholes for geothermal energy production;
   (h) in controlling zones within multiple zone oil and/or as and/or water wells;
   (i) in controlling one or more valves for regulating fluid flows; and
   (j) in chemical production apparatus for use in control of chemical injection therein.

16. A method as claimed in claim 8, said method being adapted for performing flow measurements in at least one of:
(a) down-borehole applications;
(b) in sub-sea applications;
(c) in water-injection systems;
(d) in gas-injection systems;
(e) in carbon dioxide storage systems;
(f) in oil and/or gas production;
(g) in boreholes for geothermal energy production;
(h) in controlling zones within multiple zone oil and/or as and/or water wells;
(i) in controlling one or more valves for regulating fluid flows; and
(j) in chemical production apparatus for use in control of chemical injection therein.

* * * * *

(12) EX PARTE REEXAMINATION CERTIFICATE (22nd)
Ex Parte Reexamination Ordered under 35 U.S.C. 257

United States Patent
Kippersund et al.

(10) Number: US 8,141,434 C1
(45) Certificate Issued: Jan. 30, 2015

(54) FLOW MEASURING APPARATUS

(75) Inventors: Remi Andre Kippersund, Bergen (NO); Kjell Eivind Frøysa, Fyllingsdalen (NO); Per Lunde, Sandsli (NO)

(73) Assignee: TeCom AS, Bergen (NO)

Supplemental Examination Request:
No. 96/000,051, Jun. 11, 2014

Reexamination Certificate for:
Patent No.: 8,141,434
Issued: Mar. 27, 2012
Appl. No.: 12/800,081
Filed: May 7, 2010

(30) Foreign Application Priority Data

Dec. 21, 2009 (GB) .................................. 0922466.8
Dec. 22, 2009 (NO) .................................. 20073582

(51) Int. Cl.
| | |
|---|---|
| *G01F 1/66* | (2006.01) |
| *G01F 1/42* | (2006.01) |
| *G01F 1/86* | (2006.01) |
| *G01N 9/24* | (2006.01) |
| *G01N 11/00* | (2006.01) |

(52) U.S. Cl.
CPC *G01F 1/42* (2013.01); *G01F 1/662* (2013.01); *G01F 1/667* (2013.01); *G01F 1/86* (2013.01); *G01N 9/24* (2013.01); *G01N 2011/0073* (2013.01)
USPC ...................................................... 73/861.28

(58) Field of Classification Search
None
See application file for complete search history.

(56) References Cited

To view the complete listing of prior art documents cited during the supplemental examination proceeding and the resulting reexamination proceeding for Control Number 96/000,051, please refer to the USPTO's public Patent Application Information Retrieval (PAIR) system under the Display References tab.

*Primary Examiner* — Terrence Till

(57) ABSTRACT

A flow measuring apparatus measures a fluid flow within a conduit including a wall. The apparatus includes a transducer arrangement including at least two transducers for alternately emitting and receiving ultrasonic radiation through the conduit wall and the flow. The apparatus also includes a signal processing arrangement for generating signals to excite the transducer arrangement and for processing received signals provided by the transducer arrangement for generating output signals from the signal processing arrangement indicative of properties of the flow. The transducer arrangement in cooperation with the conduit provides a first path for Lamb-wave ultrasonic radiation coupling directly from a first of the at least two transducers, to a second of said at least two transducers to generate a first received signal. The transducer arrangement in cooperation with the conduit provides at least one second path for ultrasonic propagation along the wall via Lamb waves coupling to at least a portion of the flow from a first of the at least two transducers to a second of the at least two transducers to generate a second received signal. The signal processing arrangement determines from said first and second received signals ultrasonic radiation propagation time periods through the first path and through the at least one second path, and to perform computational operations on the propagation time periods to determine properties of the flow including, but not limited to, at least one of: fluid flow velocity (v) in the conduit, a sound velocity (c) through the fluid.

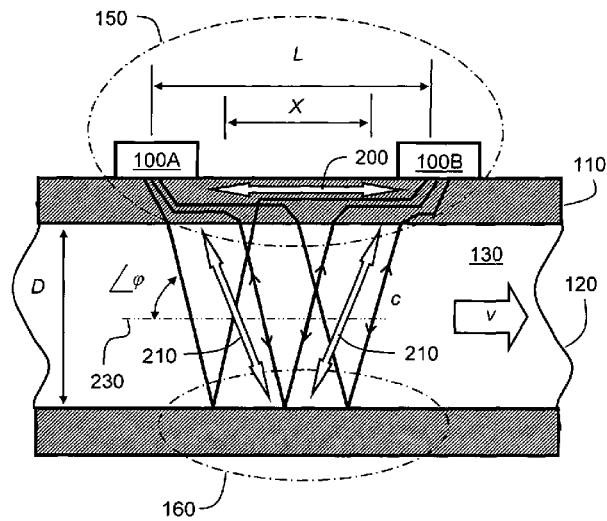

US 8,141,434 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3 and 10 are cancelled.

Claims 1 and 8 are determined to be patentable as amended.

Claims 2, 4-7, 9 and 11-16, dependent on an amended claim, are determined to be patentable.

1. A flow measuring apparatus (300, 500) for measuring a flow of a fluid (130) within a conduit (120) including one or more walls (110), said apparatus (300, 500) including a transducer arrangement (100A, 100B) including at least one transducer for emitting ultrasonic radiation into the flow (130) and at least one transducer for receiving ultrasonic radiation from the flow (130) in operation, and a signal processing arrangement (310) for generating signals to excite the transducer arrangement (100A, 100B) and for processing received signals provided by the transducer arrangement (100A, 100B) for generating output signals from the signal processing arrangement (310) indicative of properties of the flow, characterized in that said transducer arrangement (100A, 100B) in cooperation with said conduit (120) is operable to provide a first path (200) solely via said one or more walls (110) for Lamb-wave ultrasonic radiation coupling directly from the at least one transducer for emitting ultrasonic radiation to said at least one transducer for receiving ultrasonic radiation to generate a first received signal;

said transducer arrangement (100A, 100B) in cooperation with said conduit (120) is operable to provide at least one second path (210) for propagation of ultrasonic radiation within said one or more walls (100) via Lamb waves coupling to at least a portion of said flow (130) from the at least one transducer for emitting ultrasonic radiation to the at least one transducer for receiving ultrasonic radiation to generate a second received signal; and said signal processing arrangement (310) is operable to determine from said first and second signals ultrasonic radiation propagation time periods through the first path (200) and through the at least one second path (210) in upstream and downstream flow directions, and to perform computational operations on said propagation time periods to determine said properties of the flow in respect of at least one of: a flow velocity (v) of the fluid (130) in the conduit (120), a velocity of sound (c) through the fluid (130);

*wherein said propagation time periods via a plurality of said at least one second path 210 are temporally mutually similar so as to provide said signal processing unit (310) with a single temporal pulse (470) or pulse burst (470) for performing time measurements for determining said fluid flow velocity (v) and/or said velocity of sound (c).*

8. A method of measuring a flow of a fluid (130) within a conduit (120) including one or more walls (110), characterized in that said method includes:

(a) arranging for a transducer arrangement (100A, 100B) to include at least one transducer for emitting ultrasonic radiation into the flow (130) and at least one transducer for receiving ultrasonic radiation from the flow (130), and arranging for a signal processing arrangement (310) to generate signals to excite the transducer arrangement (100A, 100B) and to process received signals provided by the transducer arrangement (100A, 100B);

(b) providing for said transducer arrangement (100A, 100B) in cooperation with said conduit (120) to provide a first path (200) solely via said one or more walls (110) for Lamb-wave ultrasonic radiation coupling directly from the at least one transducer for emitting ultrasonic radiation and the at least one transducer for receiving ultrasonic radiation to generate a first received signal;

(c) providing for said transducer arrangement (100A, 100B) in cooperation with said conduit (120) to provide at least one second path (210) for propagation of ultrasonic radiation within said one or more walls (100) via Lamb waves coupling to at least a portion of said flow (130) from the at least one transducer for emitting ultrasonic radiation to the at least one transducer for receiving ultrasonic radiation to generate a second received signal; and (d) providing for said signal processing arrangement (310) to determine from said first and second signals ultrasonic radiation propagation time periods through the first path (200) and through the at least one second path (210) in upstream and downstream flow directions, and to perform computational operations on said propagation time periods to determine said properties of the flow in respect of at least one of: a flow velocity of the fluid (130) in the conduit (120), a velocity of sound through the fluid (130);

*including arranging for said propagation time periods via a plurality of said at least one second path (210) wherein said propagation time periods are temporally mutually similar so as to provide said signal processing unit (310) with a single temporal pulse (470) or pulse burst (470) for performing time measurements for determining said fluid flow velocity (v) and/or said velocity of sound (c).*

\* \* \* \* \*